(12) United States Patent
Desai

(10) Patent No.: US 11,780,092 B2
(45) Date of Patent: *Oct. 10, 2023

(54) ROBOTIC SURGICAL SYSTEM AND METHOD FOR HANDLING REAL-TIME AND NON-REAL-TIME TRAFFIC

(71) Applicant: VERB SURGICAL INC., Santa Clara, CA (US)

(72) Inventor: Jignesh Desai, Santa Clara, CA (US)

(73) Assignee: Verb Surgical Inc., Mountain View, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/711,765

(22) Filed: Apr. 1, 2022

(65) Prior Publication Data
US 2022/0226999 A1 Jul. 21, 2022

Related U.S. Application Data

(63) Continuation of application No. 16/376,193, filed on Apr. 5, 2019, now Pat. No. 11,318,618.

(51) Int. Cl.
*G05B 15/00* (2006.01)
*G05B 19/00* (2006.01)
(Continued)

(52) U.S. Cl.
CPC .............. *B25J 9/1689* (2013.01); *A61B 34/25* (2016.02); *A61B 34/30* (2016.02); *B25J 9/161* (2013.01);
(Continued)

(58) Field of Classification Search
CPC ........ A61B 2034/254; A61B 2034/301; A61B 34/25; A61B 34/30; A61B 2017/00216;
(Continued)

(56) References Cited

U.S. PATENT DOCUMENTS 7,757,028 B2   7/2010   Druke
8,072,999 B1   12/2011  Cline
(Continued)

FOREIGN PATENT DOCUMENTS

CN   101227870 A   7/2008
CN   101366010 A   2/2009
(Continued)

OTHER PUBLICATIONS

International Search Report and Written Opinion in International Application No. PCT/US2018/042922, dated Oct. 1, 2018, pp. 1-10.
(Continued)

*Primary Examiner* — Harry Y Oh
(74) *Attorney, Agent, or Firm* — Lempia Summerfield Katz LLC

(57) ABSTRACT

A robotic surgical system and method are disclosed for handling real-time and non-real-time traffic. In one embodiment, a surgical robotic system is provided comprising at least one robotic arm coupled to an operating table; and a control computer comprising a processor and a hardware interface, wherein the processor is configured to: receive a notification about real-time data from the operating table at the hardware interface; process the real-time data immediately upon receiving the notification; and poll the hardware interface for non-real time data from the operating table only when not processing the real-time data. Other embodiments are provided.

19 Claims, 10 Drawing Sheets

(51) Int. Cl.
  *B25J 9/16* (2006.01)
  *A61B 34/30* (2016.01)
  *A61B 34/00* (2016.01)
  *G16H 40/63* (2018.01)

(52) U.S. Cl.
  CPC ........ *G16H 40/63* (2018.01); *A61B 2034/254* (2016.02); *A61B 2034/301* (2016.02)

(58) Field of Classification Search
  CPC .... A61B 2034/2051; A61B 2034/2055; A61B 2034/2059; A61B 34/37; B25J 9/161; B25J 9/1689; G16H 40/63; G16H 20/40
  See application file for complete search history.

(56) References Cited

U.S. PATENT DOCUMENTS

| | | | |
|---|---|---|---|
| 8,510,491 B1* | 8/2013 | Hendel | G06F 15/17331 709/215 |
| 9,544,258 B2 | 1/2017 | Bunte | |
| 2006/0074525 A1 | 4/2006 | Close et al. | |
| 2007/0112463 A1 | 5/2007 | Roh et al. | |
| 2007/0150631 A1 | 6/2007 | Druke et al. | |
| 2008/0144526 A1 | 6/2008 | Hall | |
| 2010/0145521 A1 | 6/2010 | Prisco | |
| 2010/0234857 A1 | 9/2010 | Itkowitz | |
| 2011/0112696 A1 | 5/2011 | Yodfat et al. | |
| 2012/0039162 A1 | 2/2012 | Druke | |
| 2013/0245375 A1 | 9/2013 | Dimaio et al. | |
| 2013/0345875 A1 | 12/2013 | Brooks et al. | |
| 2014/0210520 A1 | 7/2014 | Harris | |
| 2014/0277718 A1* | 9/2014 | Izhikevich | B25J 9/163 700/250 |
| 2015/0078746 A1 | 3/2015 | Spock | |
| 2016/0034305 A1* | 2/2016 | Shear | H04L 47/70 707/722 |
| 2016/0338676 A1 | 11/2016 | Berger et al. | |
| 2017/0097631 A1 | 4/2017 | Linnell et al. | |
| 2018/0303482 A1 | 10/2018 | Shelton, IV et al. | |
| 2019/0083186 A1* | 3/2019 | Zietlow | A61B 34/37 |
| 2019/0083190 A1* | 3/2019 | Graves | H04L 12/43 |

FOREIGN PATENT DOCUMENTS

| | | |
|---|---|---|
| CN | 107615395 A | 1/2018 |
| CN | 108135666 A | 6/2018 |
| CN | 108290290 A | 7/2018 |

OTHER PUBLICATIONS

International Search Report and Written Opinion in International Application No. PCT/US2018/042930, dated Oct. 1, 2018, pp. 1-9.
International Search Report and Written Opinion in International Application No. PCT/US2019/026582, dated Jul. 9, 2019, 11 pages.
Office Action in U.S. Appl. No. 15/707,503, dated Jun. 18, 2019, 13 pages.
Chinese Office Action for Chinese Application No. 201980095086.1 dated Oct. 19, 2022, with English translation.
European Search Report for European Application No. 19923689.4 dated Dec. 8, 2022.
Ueda, K., Kikutani, T. and Yakoh, T., 2014, May. Parallel implementation of real-time communication and IP communication by using multiple ring buffers. In 2014 10th IEEE Workshop on Factory Communication Systems (WFCS 2014) (pp. 1-8). IEEE.
Zhang, Y., Gill, C. and Lu, C., 2009, August. Real-time performance and middleware for multiprocessor and multicore linux platforms. In 2009 15th IEEE International Conference on Embedded and Real-Time Computing Systems and Applications (pp. 437-446). IEEE.

* cited by examiner

ROBOTIC SURGICAL SYSTEM AND METHOD FOR HANDLING REAL-TIME AND NON-REAL-TIME TRAFFIC

RELATED APPLICATION

This application is a continuation of U.S. application Ser. No. 16/376,193, filed Apr. 5, 2019, which is hereby incorporated by reference in its entirety.

TECHNICAL FIELD

The subject technology generally relates to robotics and surgical systems, and more specifically to system architectures and components of a surgical robotic system for minimally invasive surgeries.

BACKGROUND

Minimally-invasive surgery (MIS), such as laparoscopic surgery, involves techniques intended to reduce tissue damage during a surgical procedure. For example, laparoscopic procedures typically involve creating a number of small incisions in the patient (e.g., in the abdomen), and introducing one or more surgical tools (e.g., end effectors and endoscope) through the incisions into the patient. The surgical procedures may then be performed using the introduced surgical tools, with the visualization aid provided by the endoscope.

Generally, MIS provides multiple benefits, such as reduced patient scarring, less patient pain, shorter patient recovery periods, and lower medical treatment costs associated with patient recovery. Recent technology development allows more MIS to be performed with robotic systems that include one or more robotic arms for manipulating surgical tools based on commands from a remote operator. A robotic arm may, for example, support at its distal end various devices such as surgical end effectors, imaging devices, cannulas for providing access to the patient's body cavity and organs, etc. In robotic MIS systems, it may be desirable to establish and maintain high positional accuracy for surgical instruments supported by the robotic arms.

Existing robotically-assisted surgical systems usually consist of a surgeon console that resides in the same operating room as the patient and a patient-side cart with four interactive robotic arms controlled from the console. Three of the arms hold instruments such as scalpels, scissors, or graspers, while the fourth arm supports an endoscope camera. In order to reposition the patient during a surgical procedure, surgical staff may have to undock the instruments/arms, reposition the arms/patient cart, and re-dock the instruments/arms.

DETAILED DESCRIPTION

Figure 1:
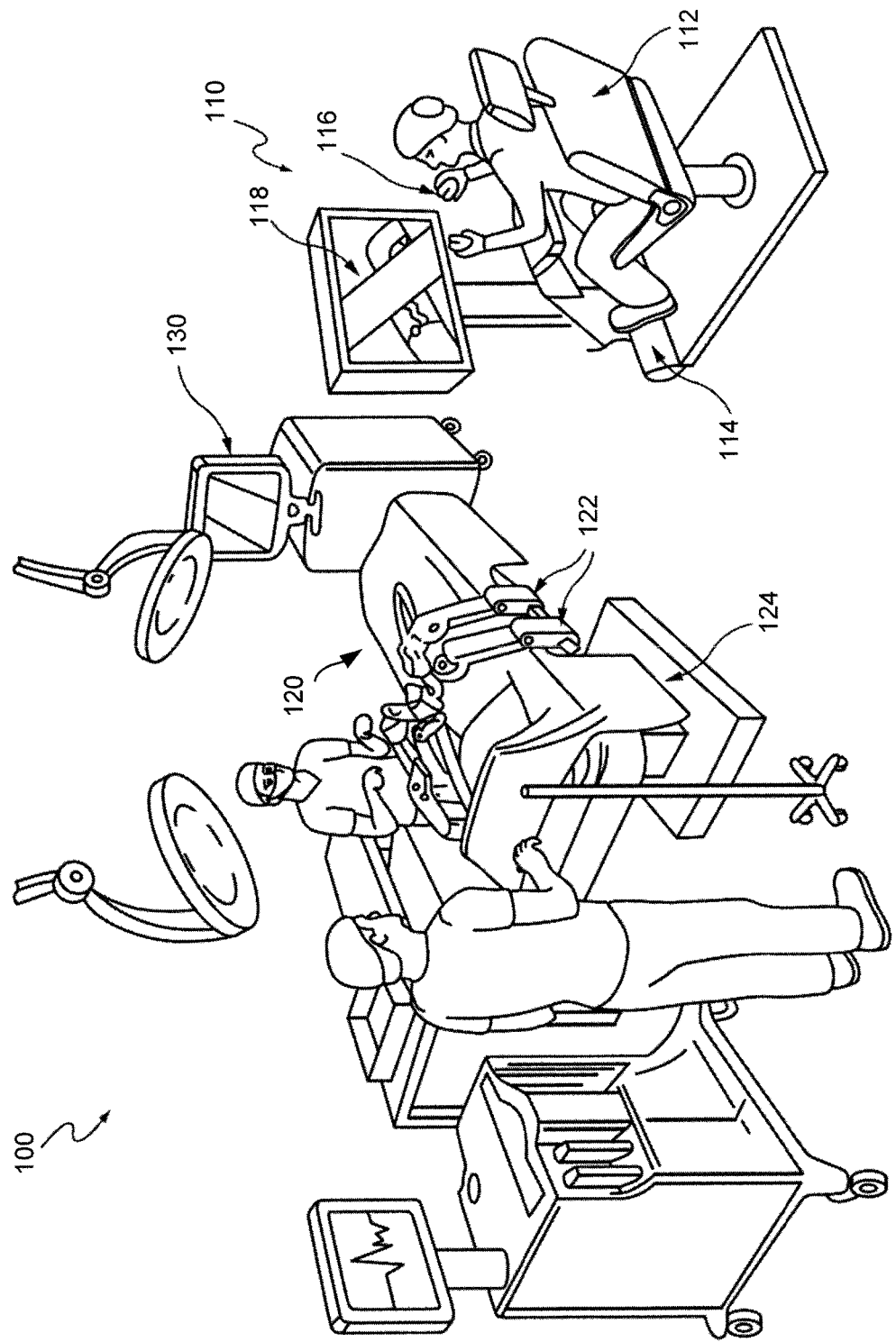
FIG. 1 is a diagram illustrating an example operating room environment with a surgical robotic system, in accordance with aspects of the subject technology.

Examples of various aspects and variations of the subject technology are described herein and illustrated in the accompanying drawings. The following description is not intended to limit the invention to these embodiments, but rather to enable a person skilled in the art to make and use this invention.

System Overview

Disclosed herein is a robotically-assisted surgical system, which is a software-controlled, electro-mechanical system, designed for surgeons to perform minimally-invasive surgery. The surgical robotic system may be comprised of three major subsystems: a surgeon subsystem—the user console (surgeon console or surgeon bridge), a central control subsystem—the control tower, and a patient subsystem—the table and robotic arms. A surgeon seated in a surgeon seat of the user console may control the movement of compatible instruments using master user input devices (UIDs) and foot pedals. The surgeon can view a three-dimensional (3D) endoscopic image on a high-resolution open stereo display, which provides the surgeon the view of the patient anatomy and instrumentation along with icons, apps, and other user interface features. The user console may also provide an option for immersive display using a periscope, which can be pulled from the back of the surgeon seat.

The control tower can function as the control and communication center of the surgical robotic system. It may be a mobile point-of-care cart housing a touchscreen display, and include computers that control the surgeon's robotically-assisted manipulation of instruments, safety systems, a graphical user interface (GUI), an advanced light engine (also referred to as a light source), and video and graphics processors, among other supporting electronic and processing equipment. The control tower can also house third-party devices like an electrosurgical generator unit (ESU), and insufflator and $CO_2$ tanks.

The patient subsystem may be an articulated operating room (OR) table with, for example, up to four integrated robotic arms positioned over the target patient anatomy. The robotic arms of the surgical system may incorporate a remote center design, i.e., each arm pivots about a fixed point in space where the cannula passes through a patient's body wall. This reduces lateral movement of the cannula and minimizes stresses at the patient's body wall. A suite of compatible tools can be attached/detached from an instrument driver mounted to the distal end of each arm, enabling the surgeon to perform various surgical tasks. The instrument drivers can provide intracorporeal access to the surgical site, mechanical actuation of compatible tools through a sterile interface, and communication with compatible tools through a sterile interface and user touchpoints. An endoscope can be attached to any arm and provide the surgeon with the high resolution, three-dimensional view of the patient anatomy. The endoscope can also be used endoscopically (hand-held) at the start of a surgery and then be mounted on any one of the four arms. Additional accessories such as trocars (also called sleeves, seal cartridge, and obturators) and drapes may be needed to perform procedures with the surgical robotic system.

The surgical robotic system can be used with an endoscope, compatible endoscopic instruments, and accessories. The system may be used by trained physicians in an operating room environment to assist in the accurate control of compatible endoscopic instruments during robotically-assisted urologic, gynecologic and other laparoscopic surgical procedures. The system also allows the surgical staff to reposition the patient by adjusting the table without undocking the robotic arms during urologic, gynecologic and other laparoscopic surgical procedures. The compatible endoscopic instruments and accessories for use with the surgical system are intended for endoscopic manipulation of tissue including grasping, cutting, blunt and sharp dissection, approximation, ligation, electrocautery, and suturing.

Turning now to the drawings, FIG. 1 is a diagram illustrating an example operating room environment with a surgical robotic system 100, in accordance with aspects of the subject technology. As shown in FIG. 1, the surgical robotic system 100 comprises a user console 110, a control tower 130, and a surgical robot 120 having one or more surgical robotic arms 122 mounted on a surgical platform 124 (e.g., a table or a bed etc.), where surgical tools with end effectors (e.g., scalpels, scissors, or graspers) are attached to the distal ends of the robotic arms 122 for executing a surgical procedure. The robotic arms 122 are shown as table-mounted, but in other configurations, the robotic arms may be mounted in a cart, a ceiling, a sidewall, or other suitable support surfaces.

Generally, a user, such as a surgeon or other operator, may be seated at the user console 110 to remotely manipulate the robotic arms 122 and/or surgical instruments (e.g., teleoperation). The user console 110 may be located in the same operation room as the robotic system 100, as shown in FIG. 1. In other environments, the user console 110 may be located in an adjacent or nearby room, or tele-operated from a remote location in a different building, city, or country. The user console 110 may comprise a seat 112, pedals 114, one or more handheld user interface devices (UIDs) 116, and an open display 118 configured to display, for example, a view of the surgical site inside a patient. As shown in the exemplary user console 110, a surgeon sitting in the seat 112 and viewing the open display 118 may manipulate the pedals 114 and/or handheld user interface devices 116 to remotely control the robotic arms 122 and/or surgical instruments mounted to the distal ends of the arms 122.

In some variations, a user may also operate the surgical robotic system 100 in an "over the bed" (OTB) mode, in which the user is at the patient's side and simultaneously manipulating a robotically-driven tool/end effector attached thereto (e.g., with a handheld user interface device 116 held in one hand) and a manual laparoscopic tool. For example, the user's left hand may be manipulating a handheld user interface device 116 to control a robotic surgical component, while the user's right hand may be manipulating a manual laparoscopic tool. Thus, in these variations, the user may perform both robotic-assisted MIS and manual laparoscopic surgery on a patient.

During an exemplary procedure or surgery, the patient is prepped and draped in a sterile fashion to achieve anesthesia. Initial access to the surgical site may be performed manually with the robotic system 100 in a stowed configuration or withdrawn configuration to facilitate access to the surgical site. Once the access is completed, initial positioning and/or preparation of the robotic system may be performed. During the procedure, a surgeon in the user console 110 may utilize the pedals 114 and/or user interface devices 116 to manipulate various end effectors and/or imaging systems to perform the surgery. Manual assistance may also be provided at the procedure table by sterile-gowned personnel, who may perform tasks including but not limited to, retracting tissues or performing manual repositioning or tool exchange involving one or more robotic arms 122. Non-sterile personnel may also be present to assist the surgeon at the user console 110. When the procedure or surgery is completed, the robotic system 100 and/or user console 110 may be configured or set in a state to facilitate one or more post-operative procedures, including but not limited to, robotic system 100 cleaning and/or sterilization, and/or healthcare record entry or printout, whether electronic or hard copy, such as via the user console 110.

In some aspects, the communication between the surgical robot 120 and the user console 110 may be through the control tower 130, which may translate user input from the user console 110 to robotic control commands and transmit the control commands to the surgical robot 120. The control tower 130 may also transmit status and feedback from the robot 120 back to the user console 110. The connections between the surgical robot 120, the user console 110 and the control tower 130 may be via wired and/or wireless connections, and may be proprietary and/or performed using any of a variety of data communication protocols. Any wired connections may be optionally built into the floor and/or walls or ceiling of the operating room. The surgical robotic system 100 may provide video output to one or more displays, including displays within the operating room, as well as remote displays accessible via the Internet or other networks. The video output or feed may also be encrypted to ensure privacy and all or portions of the video output may be saved to a server or electronic healthcare record system.

Prior to initiating surgery with the surgical robotic system, the surgical team can perform the preoperative setup. During the preoperative setup, the main components of the surgical robotic system (table 124 and robotic arms 122, control tower 130, and user console 110) are positioned in the operating room, connected, and powered on. The table 124 and robotic arms 122 may be in a fully-stowed configuration with the arms 122 under the table 124 for storage and/or transportation purposes. The surgical team can extend the arms from their stowed position for sterile draping. After draping, the arms 122 can be partially retracted until needed for use. A number of conventional laparoscopic steps may need to be performed including trocar placement and insufflation. For example, each sleeve can be inserted with the aid of an obturator, into a small incision and through the body wall. The sleeve and obturator allow optical entry for visualization of tissue layers during insertion to minimize risk of injury during placement. The endoscope is typically placed first to provide hand-held camera visualization for placement of other trocars. After insufflation, if required, manual instruments can be inserted through the sleeve to perform any laparoscopic steps by hand.

Next, the surgical team may position the robotic arms 122 over the patient and attach each arm 122 to its corresponding sleeve. The surgical robotic system 100 has the capability to uniquely identify each tool (endoscope and surgical instruments) as soon as it is attached and display the tool type and arm location on the open or immersive display 118 at the user console 110 and the touchscreen display on the control tower 130. The corresponding tool functions are enabled and can be activated using the master UIDs 116 and foot pedals 114. The patient-side assistant can attach and detach the tools, as required, throughout the procedure. The surgeon seated at the user console 110 can begin to perform surgery using the tools controlled by two master UIDs 116 and foot pedals 114. The system translates the surgeon's hand, wrist, and finger movements through the master UIDs 116 into precise real-time movements of the surgical tools. Therefore, the system constantly monitors every surgical maneuver of the surgeon and pauses instrument movement if the system is unable to precisely mirror the surgeon's hand motions. In case the endoscope is moved from one arm to another during surgery, the system can adjust the master UIDs 116 for instrument alignment and continue instrument control and motion. The foot pedals 114 may be used to activate various system modes, such as endoscope control and various instrument functions including monopolar and bipolar cautery, without involving surgeon's hands removed from the master UIDs 116.

The table 124 can be repositioned intraoperatively. For safety reason, all tool tips should to be in view and under active control by the surgeon at the user console 110. Instruments that are not under active surgeon control must be removed, and the table feet must be locked. During table motion, the integrated robotic arms 122 may passively follow the table movements. Audio and visual cues can be used to guide the surgery team during table motion. Audio cues may include tones and voice prompts. Visual messaging on the displays at the user console 110 and control tower 130 can inform the surgical team of the table motion status.

System Architecture

Figure 2:
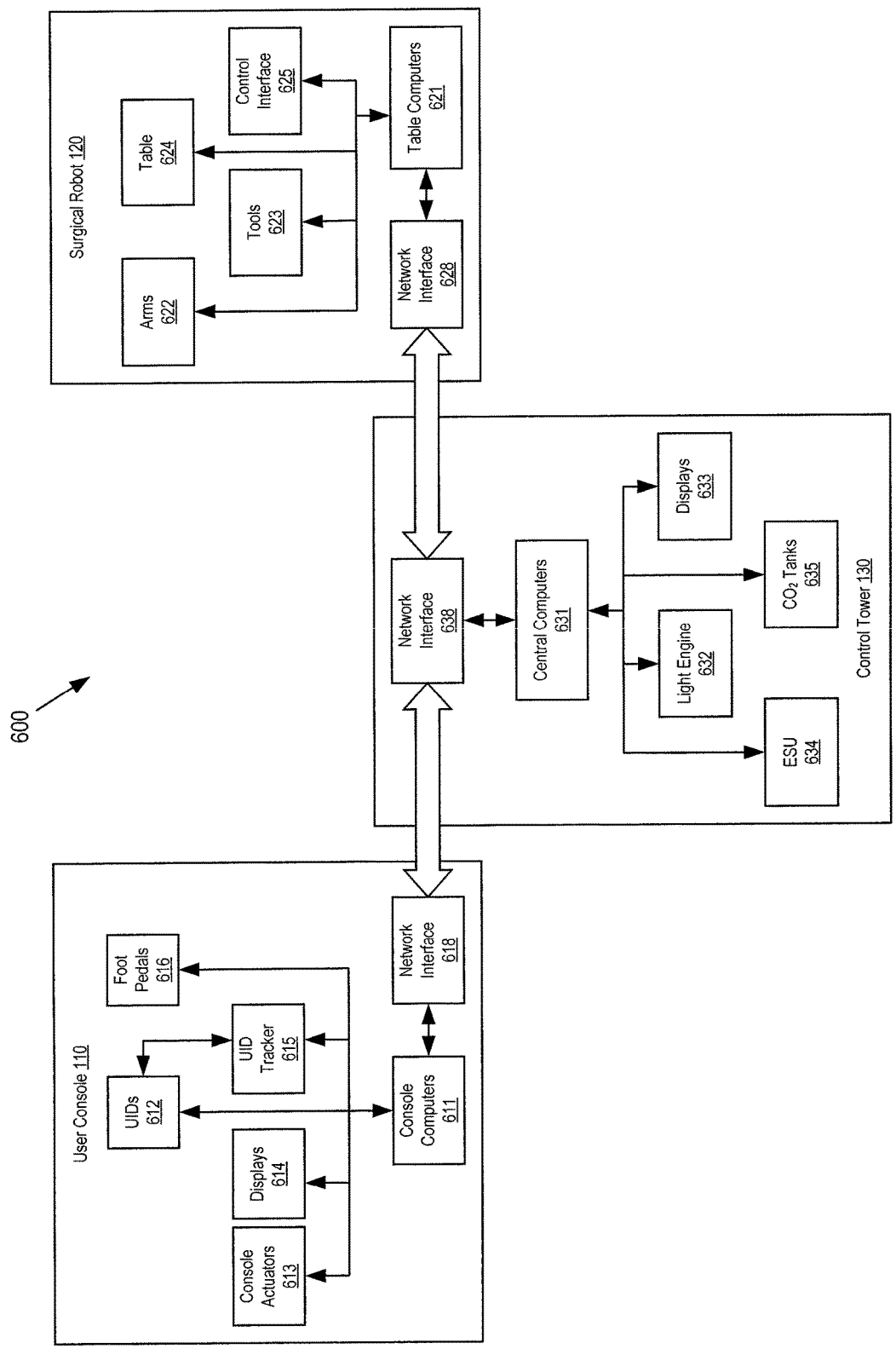
FIG. 2 is a block diagram illustrating exemplary hardware components of a surgical robotic system, in accordance with aspects of the subject technology.

FIG. 2 is a block diagram illustrating an exemplary hardware components of a surgical robotic system 600, in accordance with aspects of the subject technology. The exemplary surgical robotic system 600 may include a user console 110, a surgical robot 120, and a control tower 130. The surgical robotic system 600 may include other or additional hardware components; thus, the diagram is provided by way of example and not a limitation to the system architecture.

As described above, the user console 110 comprises console computers 611, one or more UIDs 812, console actuators 613, displays 614, a UID tracker 615, foot pedals 616, and a network interface 618. A user or surgeon sitting at the user console 110 can adjust ergonomic settings of the user console 110 manually, or the settings can be automatically adjusted according to user profile or preference. The manual and automatic adjustments may be achieved through driving the console actuators 613 based on user input or stored configurations by the console computers 611. The user may perform robot-assisted surgeries by controlling the surgical robot 120 using two master UIDs 612 and foot pedals 616. Positions and orientations of the UIDs 612 are continuously tracked by the UID tracker 615, and status changes are recorded by the console computers 611 as user input and dispatched to the control tower 130 via the network interface 618. Real-time surgical video of patient anatomy, instrumentation, and relevant software apps can be presented to the user on the high resolution 3D displays 614 including open or immersive displays.

Unlike other existing surgical robotic systems, the user console 110 disclosed herein may be communicatively coupled to the control tower 130 over a single fiber optic cable. The user console also provides additional features for improved ergonomics. For example, both an open and immersive display are offered compared to only an immersive display. Furthermore, a highly-adjustable seat for surgeons and master UIDs tracked through electromagnetic or optical trackers are included at the user console 110 for improved ergonomics. To improve safety, eye tracking, head tracking, and/or seat swivel tracking can be implemented to prevent accidental tool motion, for example, by pausing or locking teleoperation when the user's gaze is not engaged in the surgical site on the open display for over a predetermined period of time.

The control tower 130 can be a mobile point-of-care cart housing touchscreen displays, computers that control the surgeon's robotically-assisted manipulation of instruments, safety systems, graphical user interface (GUI), light source, and video and graphics computers. As shown in FIG. 2, the control tower 130 may comprise central computers 631 including at least a visualization computer, a control computer, and an auxiliary computer, various displays 633 including a team display and a nurse display, and a network interface 638 coupling the control tower 130 to both the user console 110 and the surgical robot 120. The control tower 130 may also house third-party devices, such as an advanced light engine 632, an electrosurgical generator unit (ESU) 634, and insufflator and $CO_2$ tanks 635. The control tower 130 may offer additional features for user convenience, such as the nurse display touchscreen, soft power and E-hold buttons, user-facing USB for video and still images, and electronic caster control interface. The auxiliary computer may also run a real-time Linux, providing logging/monitoring and interacting with cloud-based web services.

The surgical robot 120 comprises an articulated operating table 624 with a plurality of integrated arms 622 that can be positioned over the target patient anatomy. A suite of compatible tools 623 can be attached to or detached from the distal ends of the arms 622, enabling the surgeon to perform various surgical procedures. The surgical robot 120 may also comprise a control interface 625 for manual control of the arms 622, table 624, and tools 623. The control interface can include items such as, but not limited to, remote controls, buttons, panels, and touchscreens. Other accessories such as trocars (sleeves, seal cartridge, and obturators) and drapes may also be needed to perform procedures with the system. In some variations, the plurality of the arms 622 includes four arms mounted on both sides of the operating table 624, with two arms on each side. For certain surgical procedures, an arm mounted on one side of the table can be positioned on the other side of the table by stretching out and crossing over under the table and arms mounted on the other side, resulting in a total of three arms positioned on the same side of the table 624. The surgical tool can also comprise table computers 621 (such as a table adapter controller 700, which will be discussed below) and a network interface 628, which can place the surgical robot 120 in communication with the control tower 130.

Network Topology

Figure 3:
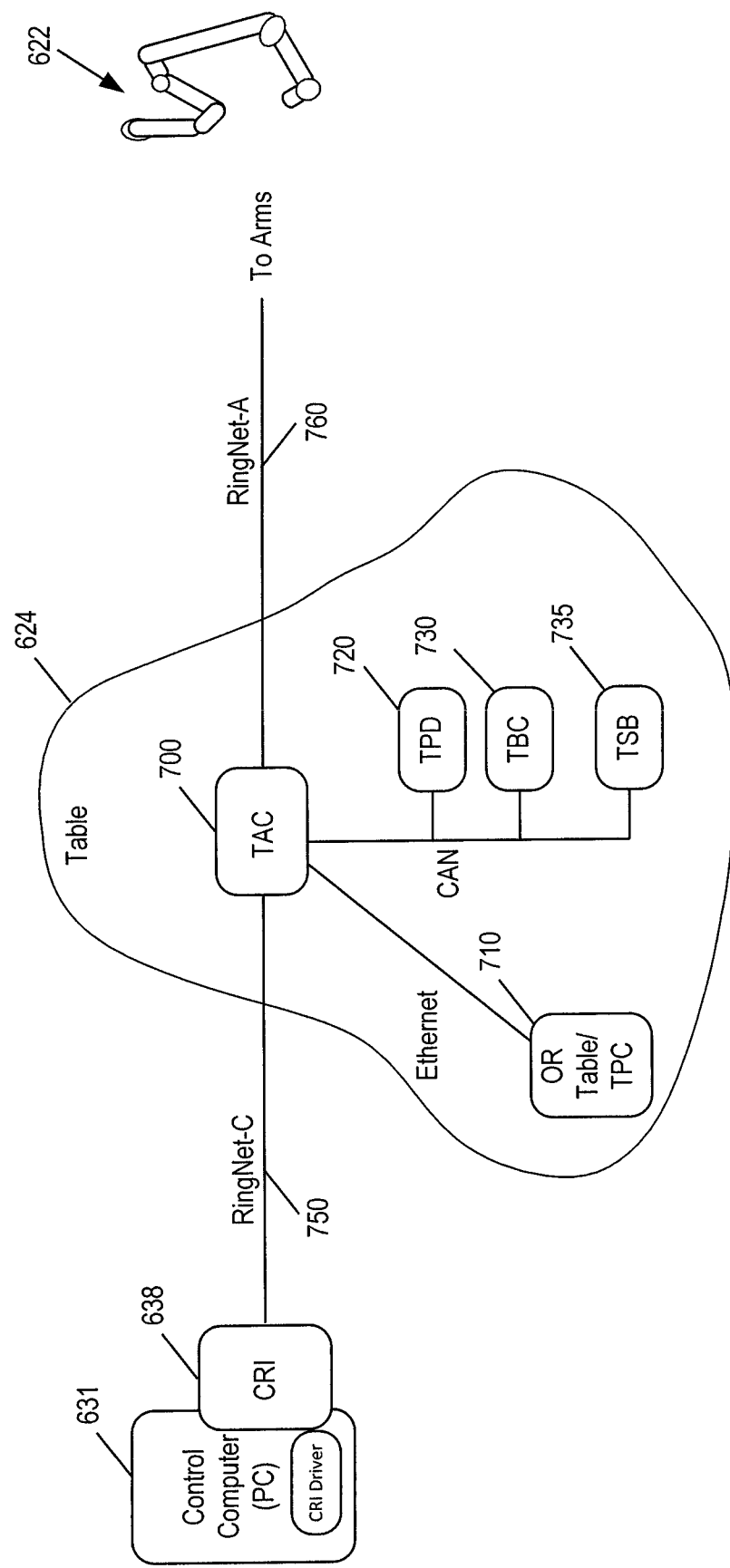
FIG. 3 is an illustration of a network topology of an embodiment.

In one embodiment, the control tower, the table controller, and the robotic arms communicate with each other over a network, such as a ring network, although other types of networks can be used. FIG. 3 is an illustration of a network topology of an embodiment. As shown in FIG. 3, the control computer 631 of the control tower uses a controller RingNet interface (CRI) 638 to communicate with the table computer (here, a table adapter controller (TAC) 700, which is also referred to herein as the "base controller") using a protocol designated herein as RingNet-C, with "C" referring to the "controller RingNet interface." The TAC 700 communicates with the robotic arms 622 using a different protocol designated herein as RingNet-A, with "A" referring to "arms." As shown in FIG. 3, the TAC 700 can also be in communication with a cluster of components (sometimes referred to herein as "the TAC cluster") of the table 624. For example, in this embodiment, the table 624 is articulated and has a drive motor controlled by a table pivot controller (TPC) 710 to tilt, move, etc. the table top. As also shown in FIG. 3, a table power distribution board (TPD) 720, a table base controller board (TBC) 730, and a table speaker board (TSB) 735 are in communication with the TAC 700 via a controller area network (CAN). Of course, other components and network protocols now existing or developed in the future can be used. The various table components in the TAC cluster will sometimes be referred to as table endpoints.

Each robotic arm in this embodiment includes a plurality of nodes between adjacent links. As used herein, a "node" can generally refer to a component that communicates with a controller of the robotic surgical system (e.g., the TAC 700). A "node," which will sometimes be referred to herein as a "joint module," can be used for actuating one link of the robotic arm with respect to another (e.g., by using a motor to move a series of pulleys and a series of bands connecting the pulleys to facilitate four-bar linkage movement). In response to commands from an external controller (discussed in more detail below), the nodes can be used to articulate the various links in the robotic arm to manipulate the arm for a surgical procedure. Examples of nodes include, but are not limited to, one or more of the following: a single motor (e.g., a servomotor, a pivot-link motor, a joint motor, and a tool drive motor), a dual motor (e.g., with a differential gear drive to combine the individual motor outputs), a wireless tool interface (e.g., a tool wireless board), a force/torque sensor (e.g., an encoder that detects and provides signals characterizing at least one of force and torque multi-directionality applied to the robotic arm between the arm links/segments), an input/output board, a component that monitors power and/or communication links, or any other component that can receive/transmit data. A node can also include various electronics, such as, but not limited to, a motor controller/driver, signal processors, and/or communications electronics on a circuit board.

It should be noted that any of the controllers can be implemented in any suitable manner. For example, a controller can take the form of processing circuitry, a microprocessor or processor, and a computer-readable medium that stores computer-readable program code (e.g., firmware) executable by the (micro)processor, logic gates, switches, an application specific integrated circuit (ASIC), a programmable logic controller, and an embedded microcontroller, for example. A controller can be configured with hardware and/or firmware to perform the various functions described below and shown in the flow diagrams. More generally, a controller (or module) can contain "circuitry" configured to perform various operations. As used herein, the term "circuitry" can refer to an instruction processor, such as a Central Processing Unit (CPU), microcontroller, or a microprocessor; or an Application Specific Integrated Circuit (ASIC), Programmable Logic Device (PLD), or Field Programmable Gate Array (FPGA); or a collection of discrete logic or other circuit components, including analog circuit components, digital circuit components or both; or any combination thereof. Circuitry may include discrete interconnected hardware components or may be combined on a single integrated circuit die, distributed among multiple integrated circuit dies, or implemented in a Multiple Chip Module (MCM) of multiple integrated circuit dies in a common package, as examples. Accordingly, "circuitry" may store or access instructions for execution or may implement its functionality in hardware alone.

Information about an example communication network of a ring topology for communicating information to and from nodes of a robotic arm can be found in U.S. patent application Ser. Nos. 15/707,449 and 15/707,503, which are hereby incorporated herein by reference.

Handling Real-Time and Non-Real Time Traffic

The control PC (master controller) 631 can communicate information with the robotic arms 622 or with the components (e.g., the TPD 720, the TBC 730, and the TSB 735) in the TAC cluster. In operation, the control PC 631 sends a frame of information to the TAC 700, and an FPGA in the TAC 700 determines whether to route that frame to the TAC cluster or to the robotic arms 622. In one embodiment, the communication between the control PC 631 and the robotic arms 622 occurs is in real time (or near real time), while the communication with the various components in the cluster connected to the TAC 700 can occur in pseudo- or non-real time. Because the robotic arms 622 are interacting with the patient, it is preferred that the command/response communication between the control PC 631 and the various nodes (e.g., DSP motor controllers) of the robotic arms 622 be unimpeded, with little or no latency and with minimum jitter. In some embodiments, the arms 622s may send an error signal if they do not receive communication from the control PC 631 in an expected amount of time. As used herein, a communication occurs in real time if the communication is received by a deadline set for receipt of that communication. Near real time refers to a communication that is may be receive outside of the deadline due to a transmission delay but is, nonetheless, acceptable.

In contrast, the communication between the control PC 631 and the TAC cluster, while important, is not as urgent. For example, hardware in the table base controller (TBC) 730 may detect that the angle of the table has changed (e.g., by detecting a change in a gravity vector) or hardware in the table power distribution (TPD) board 720 may detect an overcurrent situation in one of the robotic arms 622, and software in those components can send an alert message back to the control PC 631 (e.g., which can display the alert on the graphical user interface of the control PC 631). Again, while this information is important, it can be communicated to the control PC 631 with more latency and/or jitter than would be acceptable in the command/response communication with the robotic arms 622. Such communications can be in non-real-time or pseudo-real-time (i.e., the communication does not need to be received by a certain deadline).

As noted above, the TAC frame and the arm frames can be separate frames, with the TAC 700 routing the frame to the robotic arms 622 or to the TAC cluster, as appropriate. In one embodiment, the arm frame is a constant length frame that is transmitted by the control PC 631 every 4 kHz (250 microseconds), and the TAC frame is a variable length frame (because the control PC 631 may ask for information from the multiple end points in the TAC cluster, and the response length may vary). Again, in one embodiment, the arm frame is communicated on a real-time or near-real-time basis, and the TAC frame is communicated on a pseudo- or non-real-time basis. The arm and TAC frames can be time multiplexed in the fiber.

As will be discussed in more detail below, one embodiment separates real-time data from non-real-time data into different queues/threads to ensure real-time frames of fixed-size (vs. piggybacking non-real-time data and real-time data in a frame, which results in variable frame size and jitter in real-time data processing). Also, a single driver (operating system process) can ensure that internal scheduling (between real-time and non-real-time, interrupt/polling) is controlled by the driver itself.

Figure 4:
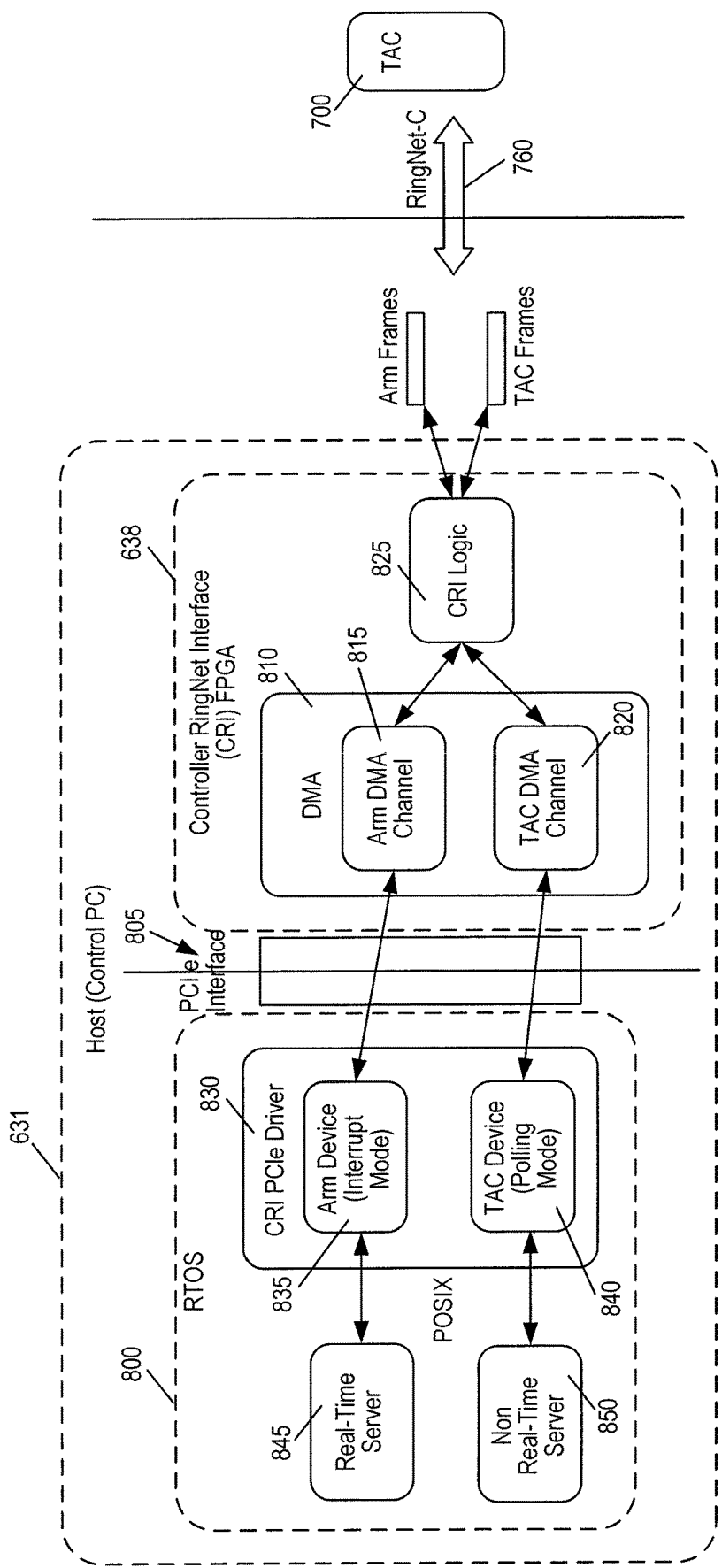
FIG. 4 is an illustration of a master controller of an embodiment.

As shown in FIG. 3, the control PC 631 is this embodiment has a controller RingNet interface (CRI) 638, which can take the form of a PCI Express card, for example. The CRI 638 has an associated driver that assists in communication, as will be discussed in more detail below. The driver can be executed in the controller computer (PC), inside the control tower, or in a backup computer inside the table (e.g., not the table PC), in case the control tower fails. FIG. 4 shows more detail one possible implementation of the arm control PC 631 (other implementations are possible). As shown in FIG. 4, in this example, the control PC 631 comprises a processor executing computer-readable program code to implement a real-time operating system 800, which communicates with the CRI 638 via a PCI Express (PCIe) Interface 805. The CRI 628 can be a card that goes into a slot in the chassis of the control PC 631. The real-time and non-real-time elements (which are elements/components of real-time and non-real-time traffic classes that run in a real-time operating system (RTOS)) 800 comprises a CRI PCIe driver 830, a real-time server 845, and a non-real-time server 850. The CRI PCIe driver 830 comprises an arm device 835 that operates in an interrupt mode and a TAC device 840 that operates in a polling mode.

As also shown in FIG. 4, the CRI 638 in this embodiment comprises a DMA component 810 with an arm DMA channel 815 and a TAC DMA channel 820. These channels 815, 820 communicate with CRI logic 825, which separates out the arm and TAC frames sent to/received from the TAC 700 via RingNet-C 760. The CRI logic 825 can also interleave and de-interleave arm frames. The arm device 835 in the driver 830 communicates with the arm DMA channel 815 in the DMA component 810 in the CRI 638, and the TAC device 40 communicates with the TAC DMA channel 820 in the DMA component 810 of the driver 830.

As shown in FIG. 4, in this embodiment, there are two independent DMA channels in the CRI FPGA, catering to two traffic classes. The multi-threaded driver talks to the channels in two separate modes: interrupt mode for the arm channel for real-time responses, and polling mode for the TAC channel for much relaxed timing constraints. The TAC channel is deliberately run at low priority, while the arm channel has highest priority. That is, the non-real-time (table controller/adapter) traffic channel is run at low priority with a pseudo-real-time, relaxed scheduling scheme, whereas the real-time (arm) traffic channel is given the highest priority with a hard real-time scheduling scheme.

The real-time server 845 in the control PC 631 is responsible sending commands and getting feedback from the robotic arms 622. The non-real-time server 850 in the control PC 631 is responsible for sending commands and getting feedback from the components in the TAC cluster. The driver 830 is responsible for ensuring that communication between the real-time server 845 and the robotic arms 622 occurs in a real-time or near-real-time basis. The driver 830 is also responsible for allowing communication between the non-real-time server 850 and the TAC cluster to occur in non-real-time or pseudo real time. In this embodiment, the driver 830 is one binary that exposes the arm and TAC channels as two devices. So, the real-time and non-real-time servers 845, 850 think they are communicating independently with two devices when, in fact, they are communicating with the same driver 830.

To achieve real-time or near-real-time communication with the robotic arms 622 (and allow pseudo- or non-real-time communication with the TAC cluster), the arm and TAC devices 835, 840 in the driver 830 operate in different modes. More specifically, the arm driver 835 operates in an interrupt mode, while the TAC driver 840 operates in a polling mode. This allows the arm and TAC traffic to be handled differently. For example, when a response is received by the CRI 638 from a robotic arm 622, the arm device 835 receives an interrupt from the CRI 638 to interrupt whatever the driver 830 is doing, so the response can be sent to the real-time server 845. Similarly, when sending a command from the real-time server 845 to the robotic arms 622, the CRI 638 sends an interrupt to the arm device 835 to interrupt whatever the driver 830 is doing, so it can be informed that the command was sent. These interruptions may mean that the processing of a communication to/from the TAC cluster is pre-empted or delayed, but that is acceptable since the TAC cluster communication does not need to occur in real- or near-real time.

In contrast to the arm device 830, the TAC device 840 operates in a polling mode. So, if a frame comes in to the CRI 638 from the TAC cluster, it is not immediately send to the driver 830, as that could possibly interrupt the driver 830 as it is processing an arm command/response, which would add delay and jitter. Instead, whenever it has time, the TAC device 840 in the driver 830 asks the CRI 838 if has any responses from the TAC cluster. If it does, the TAC device 840 will retrieve those responses and send them to the non-real-time server 850 for processing. If not, the TAC device 840 can go to sleep and awaken later to again ask the CRI 838 if has any responses from the TAC cluster. Similarly, the TAC device 840 can poll the CRI 838 to see if a command from the non-real-time server 850 was actually sent to the TAC cluster (so the driver 830 is not interrupted by an acknowledgment from the CRI 638). However, in any of these situations, if an arm command needs to be communicated, the actions of the TAC device 840 will be interrupted to allow the arm device 835 to do its work.

Figure 5:
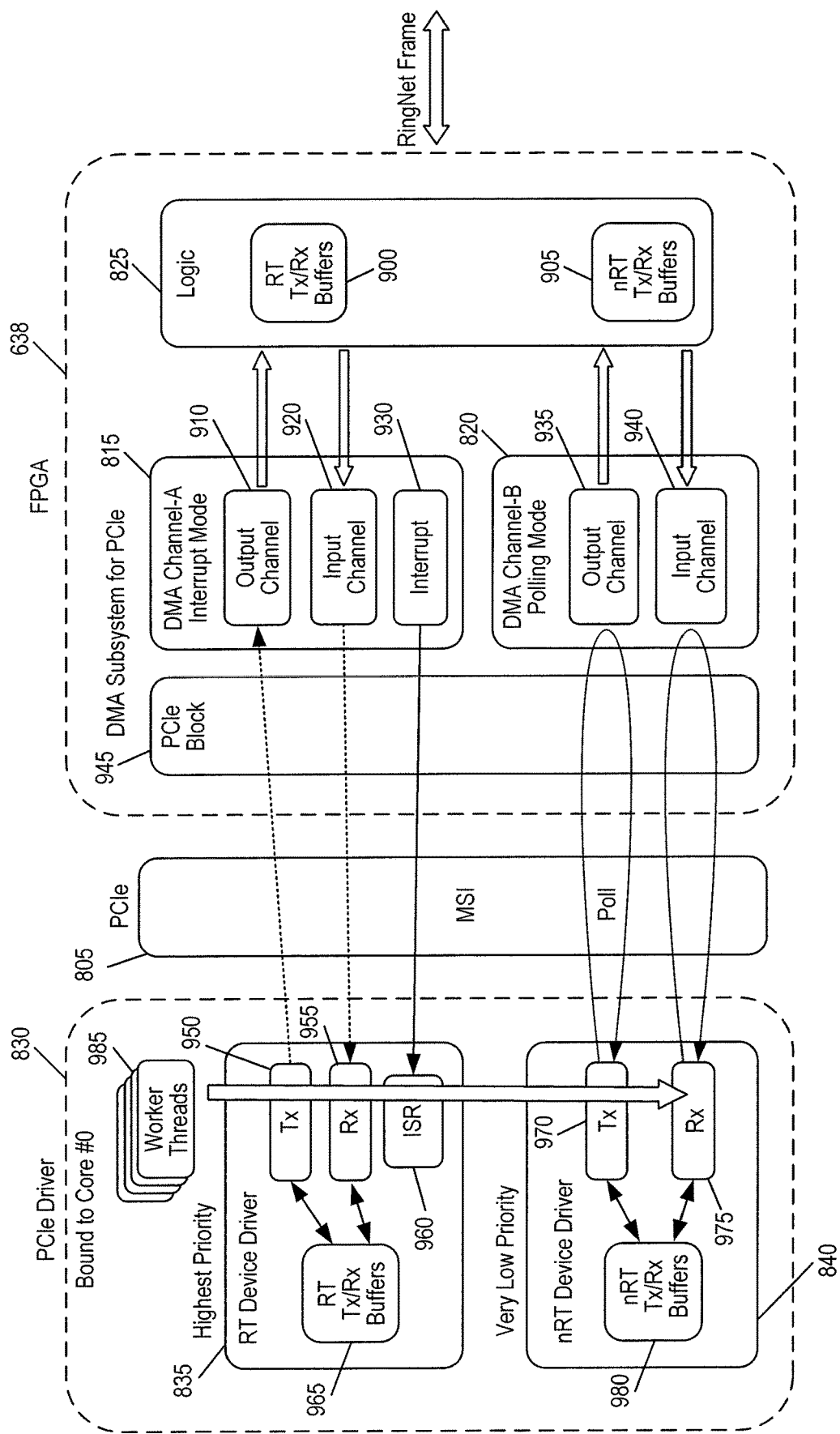
FIG. 5 is an illustration of an interaction between a driver and an interface of an embodiment.

FIG. 5 illustrates more details of the driver 830 and CRI 638 of one embodiment. As shown in FIG. 5, in this embodiment, the arm device (referred to now as the real-time device driver 835) comprises transmit and receive threads 950, 955, an interrupt service routine (ISR) 960, and real-time transmit and receive buffers 965. The TAC device (referred to now as the non-real-time device driver 840) comprises transmit and receive threads 970, 975 and non-real-time transmit and receive buffers 980. Note that the real-time device driver 835 comprises an interrupt service routine 960, whereas the non-real-time device driver 840 does not. So, the real-time device driver 835 runs at high priority (e.g., with a first-in-first-out policy), and the non-real-time device driver 840 runs at a low priority. In this embodiment, the control PC 631 has eight cores, and the real-time and non-real-time device drivers 835, 840 are bound to one of the cores. Being bound to a single core avoids thread migration across cores, which can result in latency and jitter.

As also shown in FIG. 5, in this embodiment, the CRI 638 comprises a PCIe block 945 and the arm and TAC DMA channels 815, 820, all of which are part of the PCIe and DMA component 810 (see FIG. 4). The arm DMA channel 815 (DMA Channel-A) comprises an output channel 910 (for outgoing commands to the robotic arms 622), an input channel 920 (for incoming responses from the robotic arms 622), and an interrupt routine 930. The TAC DMA channel 820 (DMA Channel-B) comprises an output channel 935 (for outgoing commands to the TAC cluster) and an input channel 940 (for incoming responses from the TAC cluster). Again, because the TAC DMA channel 820 is polled, the TAC DMA channel 820 does not have an interrupt routine. The CRI logic 825 in this embodiment comprises real-time transmit and receive buffers 900 and non-real-time transmit and receive buffers 905.

In operation, when an arm response is received by the CRI logic 825 from the robotic arms 822, the interrupt routine 930 sends an interrupt signal (e.g., a message signal interrupt (MSI)) to the ISR 960 of the real-time device driver 835 and sends the arm response to the receive thread 955 of the real-time device driver 835 via the input channel 920 of DMA Channel-A 815. The interrupt causes the driver 830 to interrupt whatever activity is currently being done by the driver 830 (e.g., processing a TAC frame), so that the real-time device driver 835 can send the response to the real-time server 845. Similarly, when the real-time server 845 sends an arm command to the real-time device driver 835, the transmit thread 950 in the real-time device driver 835 sends the command to the output channel 910 in DMA Channel-A, which sends the command to the CRI logic 825 for transmission to the TAC 700. After the command is sent, the interrupt routine 930 in DMA Channel-A 815 sends an interrupt for transmission acknowledge. In contrast, the transmit and receive threads 970, 975 in the non-real-time device driver 840 occasionally (and when the real-time device driver 835 is not active) poll the DMA Channel-B for messages received from the TAC cluster and for acknowledgements of commands transmitted to the TAC cluster. Otherwise, the non-real-time device driver 840 can go asleep. The real-time device driver 835 and the non-real-time device driver 840 may be unaware of each other. This is how the robotic surgical system provides independent and simultaneous handling of real-time and non-real-time traffic in a single PCIe driver for the controller RingNet interface (CRI) card.

Figure 6A:
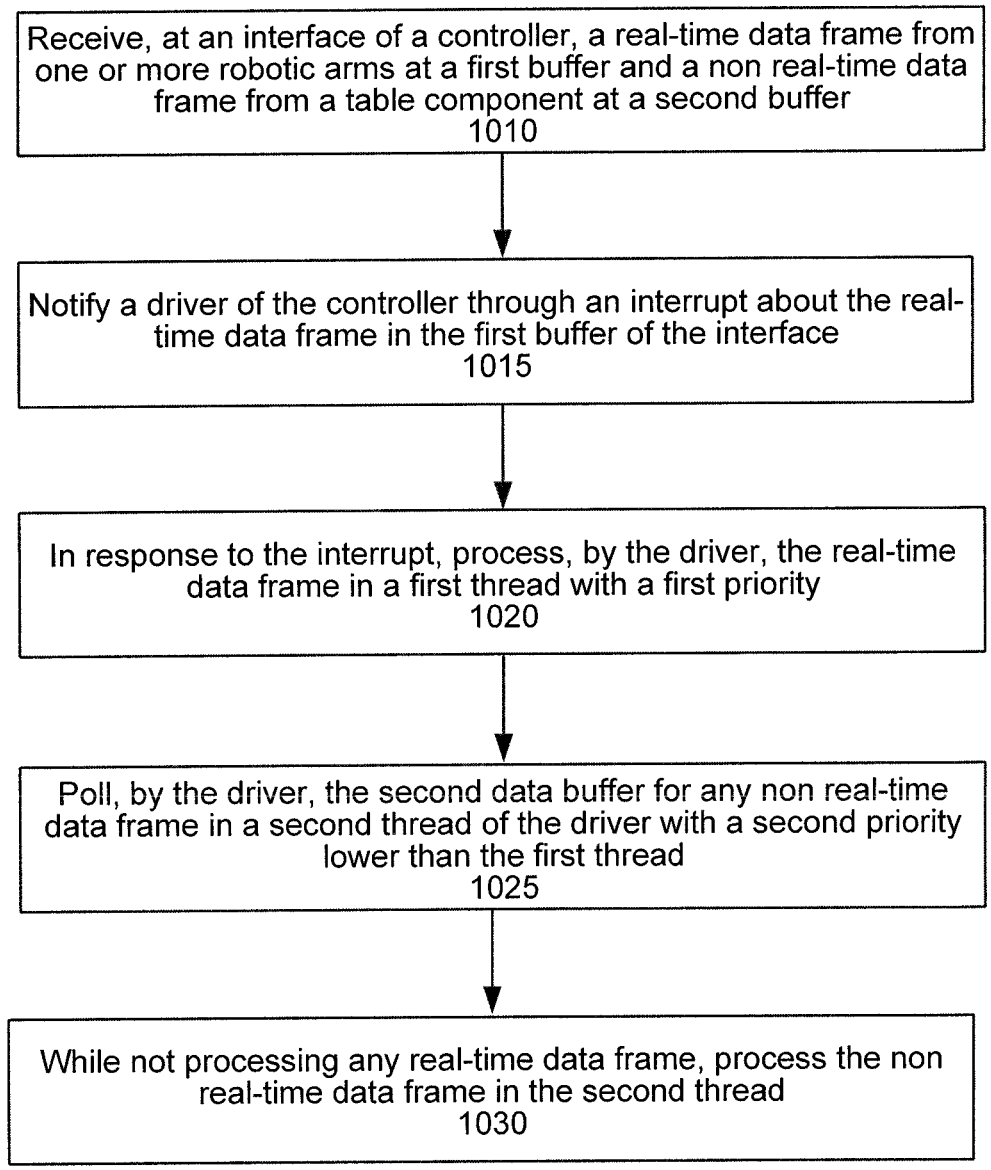
FIGS. 6A and 6B are flow charts of an embodiment for receiving and transmitting data frames.

Example methods for receiving and sending data frames will now be described in conjunction with FIGS. 6A and 6B. FIG. 6A is a flow chart of a method of an embodiment for receiving data frames by the master controller. As shown in FIG. 6A, this method comprises receiving, at an interface of the master controller, a real-time data frame from one or more robotic arms at a first buffer and a non-real-time data frame from a table component at a second buffer (act 1010). Next, a driver of the controller is notified through an interrupt about the real-time data frame in the first buffer of the interface (act 1015). In response to the interrupt, the driver processes the real-time data frame in a first thread with a first priority (act 1020). The driver then polls the second data buffer for any non-real-time data frame in a second thread of the driver with a second priority lower than the first thread (act 1025). While not processing any real-time data frame, the non-real-time data frame is processed in the second thread (act 1030).

Figure 6B:
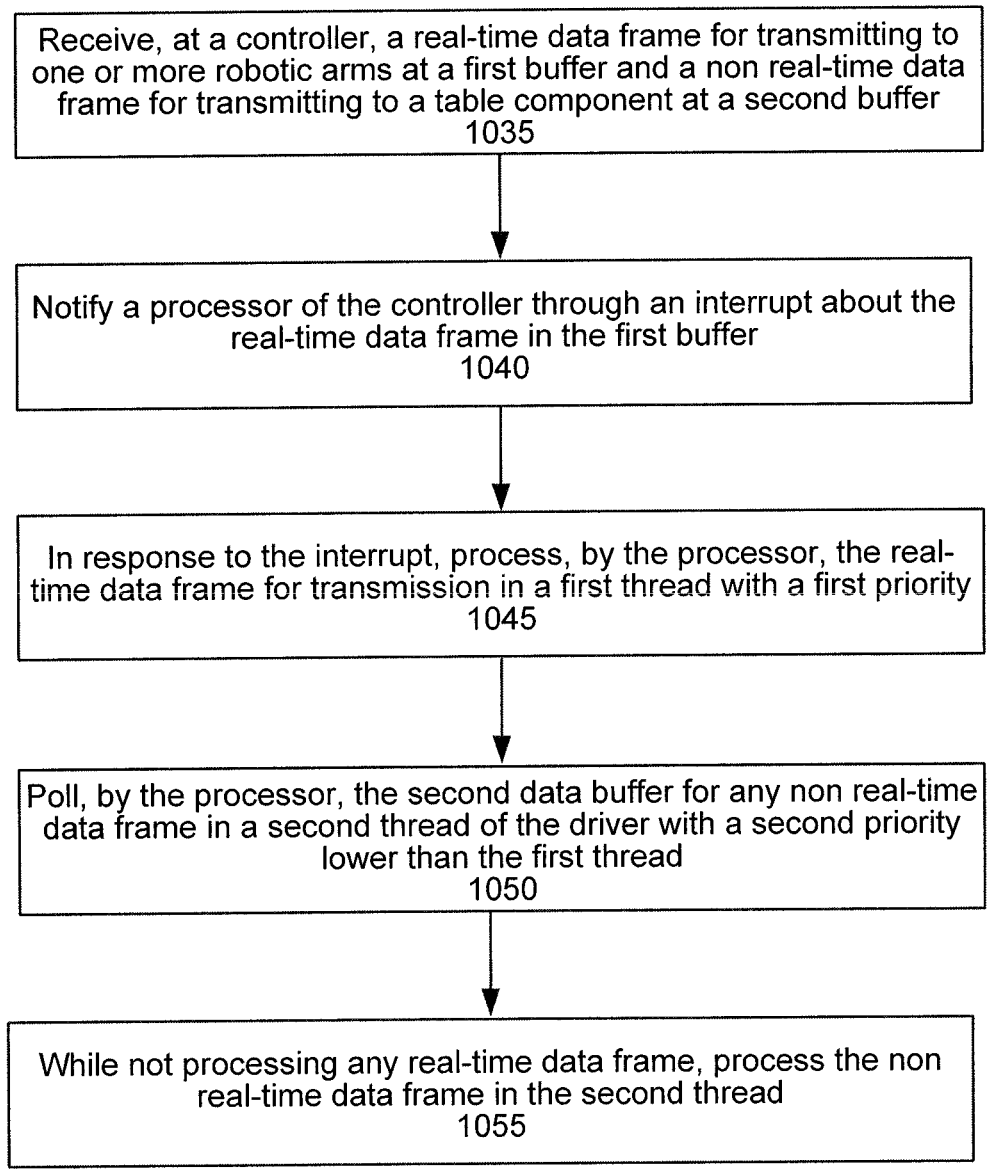

FIG. 6B is a flow chart of a method of an embodiment for sending data frames by the master controller. As shown in FIG. 6B, this method comprises receiving, at the master controller, a real-time data frame for transmitting to one or more robotic arms at a first buffer and a non-real-time data frame for transmitting to a table component at a second buffer (act 1035). Next, a processor of the controller is notified through an interrupt about the real-time data frame in the first buffer (act 1040). In response to the interrupt, the processor processes the real-time data frame for transmission in a first thread with a first priority (act 1045). The processor then polls the second data buffer for any non-real-time data frame in a second thread of the driver with a second priority lower than the first thread (act 1050). While not processing any real-time data frame, the non-real-time data frame is processed in the second thread (act 1055).

Figure 7:
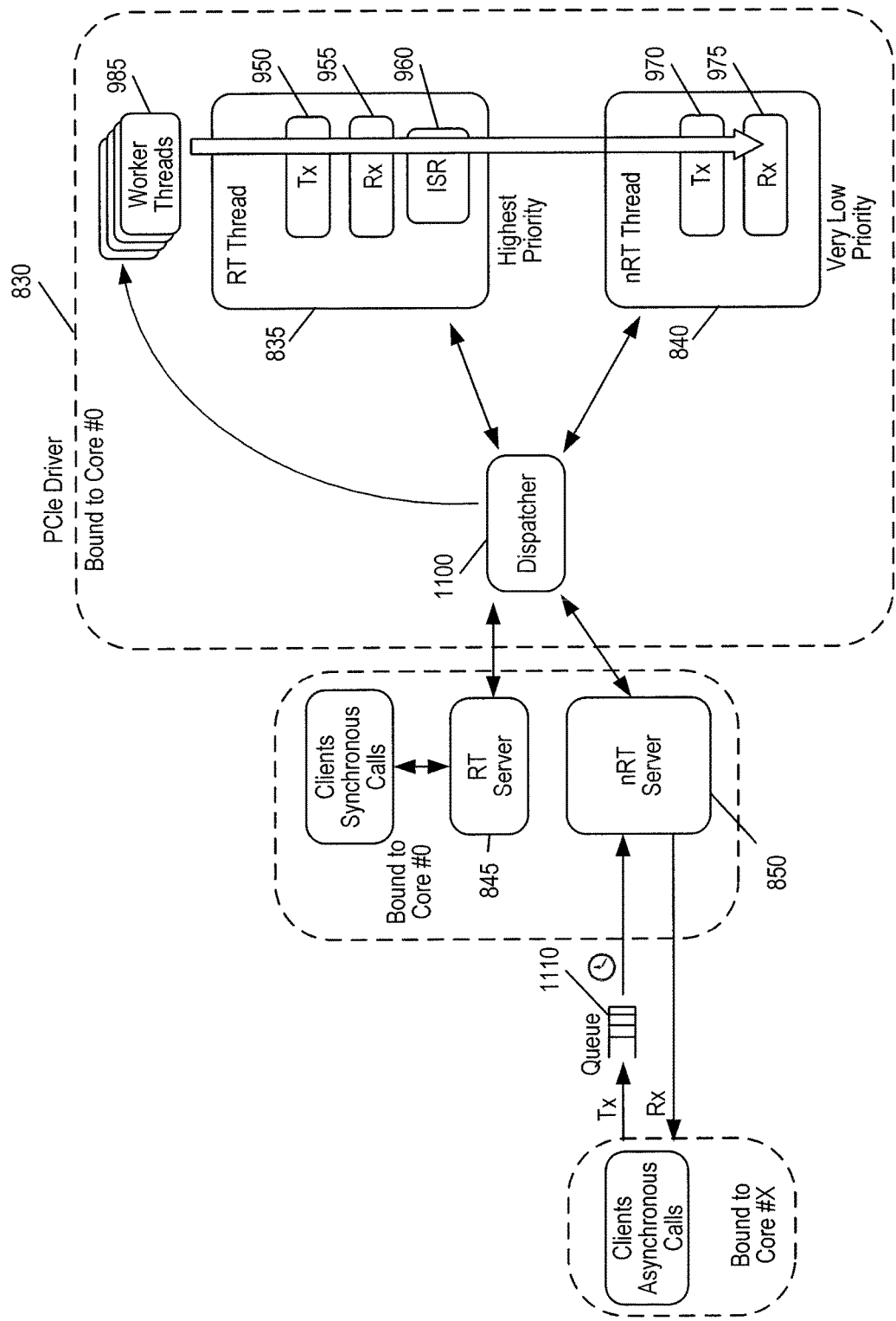
FIGS. 7 and 8 are illustrations of flow control mechanisms of an embodiment.
Figure 8:
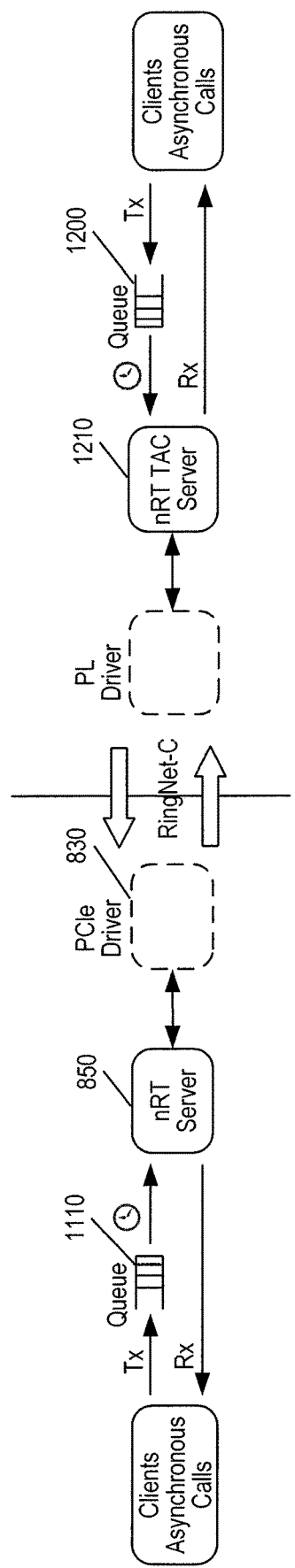

FIG. 7 illustrates a flow control mechanism of an embodiment. As shown in FIG. 7, the driver 830 comprises a dispatcher 1100, which is in communication with the real-time thread 835, the non-real-time thread 840, and the worker threads 985. The dispatcher 1100 is also in communication with the real-time and non-real-time servers 845, 850. The dispatcher 1100 controls the traffic among these components. As also shown in FIG. 7, the non-real-time server 850 uses a queue 1110 to store TAC cluster commands until the non-real-time server 850 is ready for them. This queue 1110 is desirable because TAC cluster commands are asynchronous calls. In contrast, a queue is not needed to buffer arm commands for the real-time server 845 because those commands are synchronous calls (e.g., in synch with the 4 kHz cycle). As shown in FIG. 8, a similar queue 1200 can be used for flow control to buffer asynchronous calls from the components in the TAC cluster to the non-real-time server 1210 of the TAC 700. (The programming logic (PL) driver on the table is similar to the PCIe driver 830).

Figure 9:
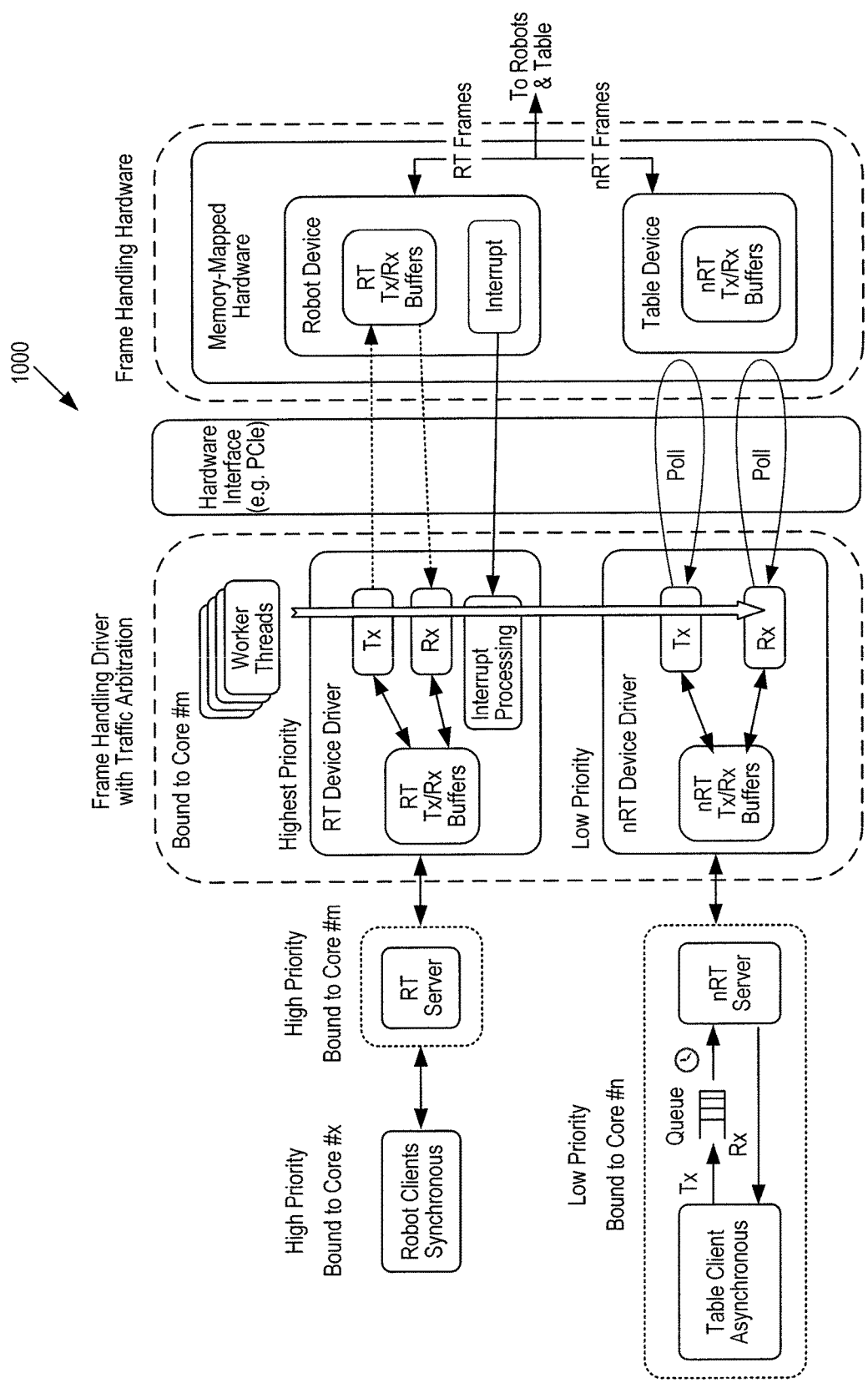
FIG. 9 is a block diagram illustrating high-level data paths of an embodiment.

FIGS. 7 and 8 show that a flow control mechanism can be applied to non real-time (table controller/adapter) traffic in transmit data paths of both directions (on the control PC and on the TAC), so that RingNet-C bandwidth can be used at a predefined rate, rather than promiscuously. This flow control mechanism avoids using unnecessary bandwidth for the non real-time traffic, by queuing all outgoing non real-time transmit frames and only presenting them to the driver at a predefined regular interval (e.g., a few orders of magnitude larger than the real-time interval of 250 uSec (4 kHz)). Further, FIG. 9 is a block diagram 1000 illustrating high-level data paths of an embodiment. In this diagram, Tx refers to transmit from host to robot/table, and Rx refers to receive from robot/table to host. Components in this drawing are similar to those discussed above.

In summary, the embodiments described herein can be used to allow the robotic surgical system to handle both real-time and non real-time traffic in a single interface driver. The driver can not only handle both traffic channels simultaneously but also can ensure that latency/jitter remains negligible for the real-time (e.g., arm) traffic while processing the non real-time (e.g., table adapter) traffic. Handling real-time and non real-time traffic from separate channels and in different drivers/processes may not be desirable because the scheduling between drivers/processes would be controlled by the operating system, which may cause unexpected delay and/or jitter to the real-time traffic.

As noted above, any suitable implementation of these embodiments can be used. The following paragraphs provide one example implementation. It should be noted that this is merely one example, and other examples can be used.

In one implementation, RingNet-C is a 1 Gbps optical communication channel between the control PC and the TAC. It carries RingNet frames for arm data, as well as TAC frames for all the data pertaining to the endpoints (TPD, TBC etc.) in table cluster. Arm frame traffic is considered hard real-time and is exchanged at the RingNet cycle rate of 4 kHz. TAC frame traffic is considered non real-time and is exchanged at its own cycle rate of 100 Hz. These two traffic classes are completely independent, but are not exclusive, and may legitimately attempt to use RingNet-C simultaneously. In this implementation, the TAC traffic neither affects the latency nor causes jitters in the arm traffic. Although these are two distinct and independent datapaths, one CRI PCIe driver supports both. This driver not only handles these two traffic channels simultaneously but also ensures that latency/jitter remain negligible for the arm traffic, while the TAC traffic is also being processed. The PCIe driver essentially hauls both arm and TAC frames from FPGA's buffers to the control PC's memory, and vice versa, while incurring negligible timing (latency/jitter) penalty for the arm traffic class.

In this implementation, there are two independent DMA channels in the CRI FPGA, catering the two traffic classes. The multi-threaded driver talks to the channels in two separate modes: interrupt mode for the arm channel for real-time responses, and polling mode for the TAC channel for much relaxed timing constraints. The TAC channel is deliberately run at low priority, while the arm channel has highest priority.

Using a single driver means one code-base, one binary for verification and validation, and one process to deploy and maintain. For the RingNet arm frame, an entire read or write operation in the driver can take ~20-30 uSec, which includes time on the wire, overheads of copying, etc. The read/write time is deducted from the total budget of 250 uSec. The TAC frame can be up to 8 kB long in one implementation. One way to approach this is to piggyback a TAC frame on an arm frame and deal with one large packet at a time, and do all this with a single DMA channel. However, if we were to piggyback the TAC frames onto the existing arm frame (making it larger), not only would the time on wire get longer, but the overhead would increase. This may require processing non real-time traffic in the real-time domain. It may be desired to avoid wasting crucial microseconds on any non real-time data, as real-time domain has a lot to accomplish within its 250 uSec (4 kHz cycle rate) budget, as described earlier. Also note that every microsecond spent in handling and hauling real-time frames is considered an overhead if the desire it to maximize the processing time given to the robotic control algorithms. Therefore, a cleaner and better approach can be to keep real-time and non real-time traffic on separate channels. To do this, two DMA channels can be employed that are controlled by a single driver with multiple threads running at different priorities. This way, the arm datapath is kept intact while simultaneously servicing the TAC datapath.

DMA transfer for arm traffic can be done using an interrupt mode to minimize latency. DMA transfer for TAC traffic is done using a polling mode, as the timing constraints are much more relaxed. To avoid disturbing the core doing real-time processing, low-priority polling can be employed on non real-time processing. The entire driver can be bound to one core of the Control PC processor. This is advantageous, as other critical real-time processes are tied to the rest of limited cores.

It may also be desirable to ensure proper prioritization of the arm over TAC frames in the driver as well as all upstream entities consuming and producing those frames. If a TAC frame transaction is ongoing and if an arm frame is detected during this time, the TAC frame transaction can be preempted. This is accomplished by combination of independent channels, multithreading, bound multi-processing, and scheduling priority/policy.

The foregoing description, for purposes of explanation, used specific nomenclature to provide a thorough understanding of the invention. However, it will be apparent to one skilled in the art that specific details are not required in order to practice the invention. Thus, the foregoing descriptions of specific embodiments of the invention are presented for purposes of illustration and description. They are not intended to be exhaustive or to limit the invention to the precise forms disclosed; obviously, many modifications and variations are possible in view of the above teachings. The embodiments were chosen and described in order to best explain the principles of the invention and its practical applications. They thereby enable others skilled in the art to best utilize the invention and various embodiments with various modifications as are suited to the particular use contemplated. It is intended that the following claims and their equivalents define the scope of the invention.

The methods, devices, processing, and logic described above may be implemented in many different ways and in many different combinations of hardware and software. The controllers and estimators may comprise electronic circuitry. For example, all or parts of the implementations may be circuitry that includes an instruction processor, such as a Central Processing Unit (CPU), microcontroller, or a microprocessor; an Application Specific Integrated Circuit (ASIC), Programmable Logic Device (PLD), or Field Programmable Gate Array (FPGA); or circuitry that includes discrete logic or other circuit components, including analog circuit components, digital circuit components or both; or any combination thereof. The circuitry may include discrete interconnected hardware components and/or may be combined on a single integrated circuit die, distributed among multiple integrated circuit dies, or implemented in a Multiple Chip Module (MCM) of multiple integrated circuit dies in a common package, as examples.

The circuitry may further include or access instructions for execution by the circuitry. The instructions may be stored in a tangible storage medium that is other than a transitory signal, such as a flash memory, a Random Access Memory (RAM), a Read Only Memory (ROM), an Erasable Programmable Read Only Memory (EPROM); or on a magnetic or optical disc, such as a Compact Disc Read Only Memory (CDROM), Hard Disk Drive (HDD), or other magnetic or optical disk; or in or on another machine-readable medium. A product, such as a computer program product, may include a storage medium and instructions stored in or on the medium, and the instructions when executed by the circuitry in a device may cause the device to implement any of the processing described above or illustrated in the drawings.

The implementations may be distributed as circuitry among multiple system components, such as among multiple processors and memories, optionally including multiple distributed processing systems. Parameters, databases, and other data structures may be separately stored and managed, may be incorporated into a single memory or database, may be logically and physically organized in many different ways, and may be implemented in many different ways, including as data structures such as linked lists, hash tables, arrays, records, objects, or implicit storage mechanisms. Programs may be parts (e.g., subroutines) of a single program, separate programs, distributed across several memories and processors, or implemented in many different ways, such as in a library, such as a shared library (e.g., a Dynamic Link Library (DLL)). The DLL, for example, may store instructions that perform any of the processing described above or illustrated in the drawings, when executed by the circuitry.

Also, the various controllers discussed herein can take the form of processing circuitry, a microprocessor or processor, and a computer-readable medium that stores computer-readable program code (e.g., firmware) executable by the (micro)processor, logic gates, switches, an application specific integrated circuit (ASIC), a programmable logic controller, and an embedded microcontroller, for example. The controller can be configured with hardware and/or firmware to perform the various functions described below and shown in the flow diagrams. Also, some of the components shown as being internal to the controller can also be stored external to the controller, and other components can be used.

What is claimed is:

1. A surgical robotic system, comprising:
    at least one robotic arm; and a control computer comprising a processor and a hardware interface, wherein the processor is configured to:
    receive a notification about real-time data from an operating table at the hardware interface; and
    poll the hardware interface for non-real-time data from the operating table only when not processing the real-time data.

2. The surgical robotic system of claim 1, wherein the real-time data comprises robotic arm traffic, and wherein the non-real-time data comprises operating table component traffic.

3. The surgical robotic system of claim 1, wherein the processor comprises a driver, and wherein the hardware interface is configured to:
    send an interrupt to the driver in response to receiving robotic arm traffic; and
    store operating table component traffic in a buffer;
    wherein the driver is configured to poll the hardware interface for the operating table component traffic when not processing the robotic arm traffic.

4. The surgical robotic system of claim 3, wherein the driver comprises a real-time device driver and a non-real-time device driver.

5. The surgical robotic system of claim 4, wherein the real-time device driver and the nonreal-time device driver are implemented with multiple threads within one driver.

6. The surgical robotic system of claim 4, wherein the real-time device driver operates in an interrupt mode, and wherein the non-real-time device driver operates in a polling mode.

7. The surgical robotic system of claim 4, wherein the real-time device driver and the nonreal-time device driver are bound to one core of the control computer.

8. The surgical robotic system of claim 4, wherein the control computer comprises a real-time server in communication with the real-time device driver and a non-real-time server in communication with the non-real-time device driver.

9. The surgical robotic system of claim 8, wherein the control computer further comprises a queue configured to store asynchronous calls before they are sent to the real-time server.

10. The surgical robotic system of claim 1, wherein the control computer is separate from an operating table.

11. The surgical robotic system of claim 10, wherein the control computer is in communication with the operating table using a first ring network protocol, and wherein the operating table is in communication with the at least one robotic arm using a second ring network protocol.

12. The surgical robotic system of claim 1 further comprising:
    a user console having one or more user interface devices, wherein the user console is configured to generate a control command for at least one robotic arm in response to manipulation of the one or more user interface devices and send the control command to the control computer, wherein the control computer is configured to translate the control command into robotic arm traffic for transmission to the operating table.

13. The surgical robotic system of claim 10, wherein the operating table comprises one or more of the following: a table power distribution board, a table base controller, and a table speaker board.

14. A method for handling data to and from a surgical robot at a control computer, the method comprising:
    receiving a notification from a hardware interface about real-time data to be forwarded to or received from a robotic arm and/or a surgical tool mounted on the robotic arm;
    and
    polling the hardware interface for non-real-time data only when not processing the real-time data.

15. The method of claim 14, wherein the controller computer comprises a driver; and wherein the hardware interface:
    sends an interrupt to the driver in response to receiving robotic arm traffic; and
    stores an operating table frame in a buffer;
    wherein the driver polls the hardware interface for the operating table frame when not processing the robotic arm traffic.

16. The method of claim 15, wherein the driver comprises a real-time device driver and a non-real-time device driver, and wherein the real-time device driver and the non-real-time device driver are implemented via two separate data paths within one driver.

17. A surgical robotic system, comprising:
    a robotic arm;
    a surgical tool coupled to a distal end of the robotic arm; and
    one or more processors configured to:
        receive a notification about real-time data for the robotic arm and the surgical tool, the notification comprising a message received by the processor where the message is for interrupt to then process the real-time data; and
        process non-real-time data for an operating table when not processing the real-time data.

18. The surgical robotic system of claim 17 further comprising a queue configured to store the non-real-time data.

19. The surgical robotic system of claim 18, wherein non-real-time data is from multiple clients.

* * * * *